United States Patent
Chernenko et al.

(10) Patent No.: US 7,087,061 B2
(45) Date of Patent: Aug. 8, 2006

(54) METHOD FOR INTRACORPOREAL LITHOTRIPSY FRAGMENTATION AND APPARATUS FOR ITS IMPLEMENTATION

(75) Inventors: Vladimir Chernenko, Toms (RU); Valeri Diamant, Katzrin (IL); Marat Lerner, Tomsk (RU); Stepan Khachin, Tomsk (RU); Vladimir Khachin, Tomsk (RU)

(73) Assignee: Lithotech Medical Ltd, Katzrin (IL)

( * ) Notice: Subject to any disclaimer, the term of this patent is extended or adjusted under 35 U.S.C. 154(b) by 161 days.

(21) Appl. No.: 10/094,797

(22) Filed: Mar. 12, 2002

(65) Prior Publication Data

US 2003/0176873 A1 Sep. 18, 2003

(51) Int. Cl.
A61B 17/22 (2006.01)
(52) U.S. Cl. ......................... 606/127; 604/22
(58) Field of Classification Search ........... 606/2.5, 606/107, 127, 128, 170, 32, 41, 45–47, 113, 606/114; 604/164.01, 200, 22, 27, 127; 128/898
See application file for complete search history.

(56) References Cited

U.S. PATENT DOCUMENTS

| | | | | |
|---|---|---|---|---|
| 2,559,227 A | * | 7/1951 | Rieber | 601/4 |
| 3,982,541 A | * | 9/1976 | L'Esperance, Jr. | 606/3 |
| 4,308,905 A | | 1/1982 | Gallagher | |
| 4,605,003 A | * | 8/1986 | Oinuma et al. | 606/128 |
| 4,722,340 A | * | 2/1988 | Takayama et al. | 601/4 |
| 4,927,427 A | * | 5/1990 | Kriauciunas et al. | 606/128 |
| 5,254,121 A | | 10/1993 | Manevitz et al. | |
| 5,448,363 A | | 9/1995 | Hager | |
| 5,722,980 A | | 3/1998 | Schulz et al. | |
| 6,149,656 A | * | 11/2000 | Walz et al. | 606/128 |
| 6,261,298 B1 | | 7/2001 | Irion et al. | |
| 6,319,261 B1 | | 11/2001 | Bowers | |

FOREIGN PATENT DOCUMENTS

| | | |
|---|---|---|
| CA | 2104414 | 2/1995 |
| DE | 3633527 | 4/1988 |
| DE | 3927260 A1 | 2/1991 |
| DE | 19609019 A1 | 9/1997 |
| DE | 19810696 C1 | 5/1999 |

OTHER PUBLICATIONS

Nortech Technologies Inc., The AUTOLITH® Lithotriptor, © 1999 Northgate Technologies, Inc., 2 pgs.
B.V. Semkin, A.F. Usov, V.I. Kirets., The Principles of Electric Impulse Destruction of Materials, Russian Academy of Sciences, 1995. (with translation), 8 pgs.
Richard Wolf, Riwolith 2280, for Electrohydraulic Shock Wave Lithotripsy, 1 pg. undated.
Riwolith 2280, Instruction Manual, HA-D257/Index: 10-00-9.0 / AM: KG 00-248, 8 pgs. undated.

(Continued)

*Primary Examiner*—Julian W. Woo
*Assistant Examiner*—Victor Nguyen
(74) *Attorney, Agent, or Firm*—Blank Rome LLP

(57) ABSTRACT

Electro-impulse intracorporeal lithotripsy comprises bringing electrodes of a probe in immediate electrical contact with the calculus and supplying to the electrodes of very short high voltage impulses capable to ignite electrical spark discharge and establish a discharge channel within the bulk of the calculus. The channel goes through the calculus and creates tensile stresses, destroying the calculus.

9 Claims, 10 Drawing Sheets

OTHER PUBLICATIONS

Russian Academy of Sciences International Associate of Scientific Discoveries Authors, Diploma No. 107, for the discovery Regularity of Solid Dielectric Breakdown at the Interface With Liquid Dielectric Under Action of Voltage Pulse Instruction Manual, 5 pgs. (Russian and English translation).

* cited by examiner a)

b)

c)

a)

b)

METHOD FOR INTRACORPOREAL LITHOTRIPSY FRAGMENTATION AND APPARATUS FOR ITS IMPLEMENTATION

FIELD OF THE INVENTION

The present invention relates to lithotripsy fragmentation of stones, appearing in a human body and in particular to so-called intracorporeal lithotripsy, during which fragmentation is caused by operation of the lithotriptor working element within the body. The present invention refers also to an apparatus for fragmentation, disintegrating or otherwise destroying the stones, e.g. gallstones, kidney stones, cystine stones and other calculi, appearing in the biliary or urinary system of a human body.

It should be understood however that the present invention is not limited to the fragmentation of calculi, appearing in the human body. It can be also employed for lithotripsy treatment of animals as well.

Furthermore the present invention is not limited to destroying of calculi appearing in merely biliary or urinary systems. It is suitable for fragmentation of any foreign objects, which might appear in other locations of the body, e.g. in blood vessels etc.

BACKGROUND OF THE INVENTION

Shock-wave lithotripsy stone fragmentation treatment employs high-energy shock waves to fragment and disintegrate calculi and it can be broadly categorized according to the pattern of energy transfer to the calculi. In this connection lithotripsy can be classified as extracorporeal and intracorporeal. The comprehensive overview of various lithotripsy methods can be found in various sources, e.g. in the Internet site http://www.bsci.com. In accordance with the acceptable definitions shock-wave extracorporeal lithotripsy is a process, which transfers energy needed for stone fragmentation in the form of shock waves from an outside source through body tissue to the calculi. Extracorporeal shock wave lithotripsy (ESWL) has proven effective in achieving stone fragmentation. However, since the energy wave transmission is indirect, and in order to carry out the treatment successfully it is required precise directional focusing of the energy at the stone through intervening body tissue. This might be associated with damaging of the intervening tissues and therefore additional treatments might be required to take care of the damage.

Intracorporeal lithotripsy utilizes a probe advanced with the aim of endoscope and positioned in proximity to the calculus. The energy, required for fragmentation is transferred through the probe to the calculus and the treatment process is visualized during fragmentation. The mode of energy transfer may be different and accordingly the intracorporeal lithotripsy techniques are divided into following groups: ultrasonic, laser, electro-hydraulic and mechanic/ballistic impact.

The last group comprises, for example, detonating an explosive near the stone and causing the shock wave generated by the explosion to act directly upon the stone and crush it into pieces. An example of such technique is disclosed in U.S. Pat. No. 4,605,003, referring to a lithotriptor comprising an inner tube inserted within an outer slender tube and provided with an explosive layer or a gas-generating layer. By the blasting of the explosive layer or the gas-generating layer, the outer slender tube or the inner tube is caused to collide with the stone and crush it.

An example of mechanical impact technique can be found in U.S. Pat. No. 5,448,363 in which is disclosed an endoscopic lithotriptor provided with a hammer element to periodically strike the stone. The hammer element is pneumatically driven by a linear jet of air causing it to swing through an arc about a pivot to impact an anvil.

There are known also many other patents, disclosing lithotriptors, which operation is based on mechanic/ballistic principle, e.g. U.S. Pat. Nos. 5,722,980, 6,261,298.

An example of laser technique is described in U.S. Pat. No. 4,308,905, concerning multi-purpose lithotriptor, equipped with laser light-conducting fibers, through which the energy required for crushing the stone is conducted.

Ultrasonic technique is relatively popular and because of its safety and usefulness is widely accepted. According to this principle ultrasound probe emits high-frequency ultrasonic energy that has a disruption effect upon direct exposure to the stone. Direct contact of the probe tip and stone is essential for effectiveness of ultrasonic lithotripsy. This technique is implemented in many lithotriptors, e.g. as described in U.S. Pat. No. 6,149,656.

The most relevant to the present invention is electro-hydraulic technique, which utilizes electric discharge, ignited between two electrodes disposed within the probe and producing shock wave, expanding towards the calculus through liquid phase, which surrounds the calculus. In the literature electro-hydraulic lithotripsy is defined as the oldest form of "power" lithotripsy. The electro-hydraulic lithotriptor releases high-energy impulse discharges from an electrode at the tip of a flexible probe, which is placed next to the stone. It is considered as highly effective means of bladder stone shattering and has become an accepted practice for this use. Since the generated during electro-hydraulic lithotripsy treatment shock waves are of sufficient force the probe must not be used 5 mm or closer to soft tissues otherwise severe damage will result.

Since the discharge takes place within liquid phase the calculus is destroyed by virtue of combination of energy of the shock wave, caused by the discharge, hydraulic pressure of the surrounding liquid and collision of fragments in the liquid flow. Below are listed some references, referring to intracorporeal lithotripting devices, utilizing the electro-hydraulic principle.

A typical electro-hydraulic lithotriptor is described in CA 2104414. This apparatus is intended for fracturing deposits such as urinary and biliary calculi as well as arteriosclerotic plaque in the body. The lithotriptor comprises a flexible elongated guide member adapted for insertion within the body, means for supplying a working fluid, a hollow tube mounted on the distal end of the probe, means for initiating an electric spark within the hollow tube from an external energy source, capable of generating pulsed shock waves in the working fluid for impinging the stone and a nozzle, which is made of shock and heat resistant material and mounted on the distal end of the guide member. The nozzle is capable of directing the shock waves to a focal point for impinging the stone. The lithotriptor is provided also with optical viewing system.

In U.S. Pat. No. 2,559,227 is disclosed an apparatus for generating shock. The apparatus comprises a truncated ellipsoidal reflector for reflecting the shock waves and a cavity constituting a chamber for reflecting said shock waves. The cavity has the same truncated ellipsoidal shape, while one of the two focal points of the ellipsoid being disposed in the cavity opposite the truncated part. The cavity is filled with a liquid for transmitting the shock waves, for example oil. The apparatus is provided with a shock wave generator device, conventionally comprising two electrodes disposed at least partly inside said cavity. The two electrodes are arranged to generate an electric arc discharge at the focal point located in the cavity opposite the truncated part. The apparatus has also means for selectively and instantaneously delivering an electric voltage to said two electrodes provoking electric arc discharge between said electrodes thus generating shock waves propagating through the liquid contained in the cavity. The electrodes are made of highly conductive material such as copper or brass and are mounted on an insulator with possibility for adjusting the spacing therebetween.

In DE 19609019 is described an impact probe, provided with at least one electrode guided in the tube. The electrode acts on the object when the probe is longitudinally moved in the direction of the object e.g. a stone. Electro-hydraulic pressure wave is produced at the free end of the probe.

It should be stressed that since the probe in conventional electro-hydraulic lithotriptors is not in physical contact with the calculus many efforts are undertaken to focus the maximum of discharge energy immediate on the calculus. An example of such an attempt is electro-hydraulic lithotriptor, known under the trade name THE AUTHOLITH and manufactured by Northgate Technologies. It should be noted, however, in this lithotriptor the energy of shock wave still is transferred via a layer of liquid, remaining between the discharge gap of the probe and the calculi.

The efficiency of electro-hydraulic lithotriptor in terms of its ability to fragment a calculus depends on voltage and duration of electrical pulses, required for achieving breakdown and initiating the spark discharge, since these parameters are interrelated with the amount of energy, which can be produced by the lithotriptor. Commercially available electro-hydraulic lithotriptors, e.g. lithotriptor RIVOLITH 2280 manufactured by Richard Wolf, are provided with pulse generators, capable to generate pulses with pulse rise time of about hundreds nanoseconds and pulse duration of about hundreds of microseconds.

It can be easily appreciated that since the energy is transferred not immediate to the calculus but via a liquid medium, the amount of energy required for fragmentation should be sufficient to overcome the strength of the calculi and to cause its failure after the energy has been delivered through the working liquid (water or urea or physiologic solution). Electric pulses having duration parameters of commercially available lithotriptors allow producing rather high energies of about 2.5–3 joule, which is sufficient for producing stresses capable to fragment various calculi, appearing in the human body.

Unfortunately, release of such high levels of energy by producing shock waves might be harmful to the adjacent tissues and therefore potentially dangerous for the patient.

The further disadvantage of the known in the art electro-hydraulic lithotriptors is associated with their inability to detect and monitor the onset of fragmentation. Since the pulse generator continues to generate pulses after the calculus has been already fragmented, unnecessary energy is produced and its release unnecessary endangers the patient.

Still further drawback of the electro-hydraulic lithotriptors is associated with the necessity to have numerous electric discharges when it is required to destroy especially large and dense calculus. Since the discharge takes place on the surface of the probe insulation, it deteriorates the insulation of the probe tip and may cause its failure even before the treatment session is completed.

Still another problem of almost all intracorporeal lithotriptors that are intended for destroying renal calculi by bringing mechanical energy of impact or shock wave is the fact that the stone is usually "displaced" with each pulse of energy, leaving the previous place and being "thrown" to another one. This renders the operation complicate and may cause mechanical damage to the surrounding tissue. Physical "anchoring" of the treated stone would be desirable here.

An attempt to solve this problem and to extend service life of the probe and at the same time to improve treatment efficiency without rise of harm to the patient is disclosed in DE 3927260. In this patent is described a probe for electrohydraulic lithotripsy, which is provided with a head made of impact-resistant ceramic in the form of a round bass-rod. The rod has two longitudinal channels into which leads are inserted and anchored by a resin material, the ends of the leads being flush with the end face of the rod. Leads pass to a plug via a flexible hose, which extends over the head.

Nevertheless, this particular solution is not designed for immediate physical contact between the probe tip producing a shockwave and the calculus.

There are known lithotriptors, in which such "anchoring" is possible, e.g. a combined holding and lithotripsy instrument, disclosed in DE 19810696. This combined instrument consists of a highly elastic NiTi alloy and has at least three holding arms, which in their unflexed state are curved in a tulip-like manner. The end of each holding arm is toothed and bent towards the instrument axis. When the holding arms are drawn into the instrument tube or working channel they position themselves on the calculus and grasp it when they are drawn in even further. The holding device is configured around the instrument axis in such a way that the angle between directly adjacent holding arms is never equal to or greater than 180 DEG C. This ensures secure holding and grasping and thus prevents the grasped calculus from escaping sideways. The securely held calculus can then be fully fragmented to fragments of a predetermined size using the lithotriptor, i.e. either mechano-ballistically, or by ultrasound, cryogenically or thermally with laser light.

Unfortunately this construction is not suitable for electro-hydraulic mode of operation since the probe tip is not designed to carry electrodes provided with electric insulation and is not therefore capable of producing shock waves, caused by electrical discharge.

On the other hand there is known for some time a method of so-called high-power electro-impulse destruction of materials, which is based on the fact that applying of electrical impulses with the rise time of not more than 500 nanoseconds to two electrodes positioned on a solid mineral material immersed in water is associated with producing discharge, which does not propagate through the surrounding liquid medium, but rather through the bulk of the solid body. This technology was developed in late fifties in Russia and since then it has been successfully implemented in such fields like crushing and disintegration of hard rocks and ores in mining industry, destructing of concrete blocks in building industry, drilling of frozen ground and extremely hard rocks, crushing of various inorganic materials, etc.

A survey of this technology can be found in a monograph "Basics of electro-impulse destroying of materials", by Semkin et al., Sanct-Petersburg, Nauka, 1993.

According to this technology two or more electrodes are placed immediate on the surface of a solid body (rock) and very short impulses of voltage U(t) are sent through them. Once an electrical breakdown between the electrodes is initiated, it occurs in the bulk of the solid body and is associated with producing of the breakdown discharge channel that extends within the bulk of the body. The body itself serves as a medium to promote propagation of the electrical breakdown rather than the surrounding medium. Extension of the discharge channel through the body is accompanied by mechanical stresses, which stretch the body and destroy it as soon as the tensile strength of the body is exceeded. In fact in the process of electro-impulse destroying the initiation and propagation of the discharge is similar to a micro explosion within the body. It can be readily appreciated that since tensile strength of a rock is at least an order of magnitude less than its compressive strength, the electro-impulse crushing is associated with consumption of much less energy, than conventional electro-hydraulic crushing.

It has been also empirically established, that the probability of propagation of the breakdown channel through the body is higher when a very short voltage impulses are applied to electrodes, positioned on a solid body immersed in a liquid medium, since the voltage required for the breakdown within the bulk of the body is less, than the voltage required for breakdown within the liquid medium outside of the body.

Unfortunately despite the fact that this technology exists for more than 40 years it still has been employed mainly in mining and building industry for destruction of very large objects like rocks or concrete blocks.

An example of this application is disclosed in WO 9710058, in which is described method of comminuting and crushing solids, for example, blocks of reinforced concrete. In accordance with this method the solid is exploded as a result of shock waves being produced therein.

Unfortunately the obvious benefits of this technology associated with more efficient destruction were never considered for employing in such completely new application, like medicine in general and intracorporeal lithotripsy in particular.

In conclusion it should be emphasized that despite the fact that numerous lithotriptors have been devised there is still a need for a new approach that will ensure efficient, reliable, easy and safe fragmentation of calculi during intracorporeal lithotripsy.

OBJECT OF THE INVENTION

The main object of the present invention is to provide a new and improved method and device for intracorporeal lithotripsy enabling to reduce sufficiently or overcome the above-mentioned drawbacks of the known in the art solutions.

In particular the first object of the invention is to provide a new and improved method and apparatus for intracorporeal lithotripsy, ensuring applying tensile stresses to calculi, appearing in the living body, instead of compressive stresses.

Still further object of the invention is to provide a new and improved method and apparatus for intracorporeal lithotripsy treatment enabling to reduce probability for traumatizing of adjacent body tissues during the treatment.

Another object of the invention is to provide improved method and apparatus for intracorporeal lithotripsy enabling to detect the onset of the fragmentation process and to terminate further generation of high voltage pulses.

Still further object of the invention is to provide improved method and apparatus for intracorporeal lithotripsy enabling easy and fast fragmentation and at the same time reliable grasping and containment of the calculus being destroyed during the treatment.

The above and other objects and advantages of the present invention can be achieved in accordance with the following combination of its essential features, referring to different embodiments thereof as a method for intracorporeal lithotripsy and as an apparatus for implementation of the method.

According to the embodiment of the invention, which refers to the method it comprises bringing a probe to the calculus to be fragmented, said probe is provided with electrodes, connected to a means for generating of high voltage impulses, said impulses are supplied to the electrodes for igniting spark discharge between them and release of energy, causing fragmenting of the calculus, wherein the method comprises bringing of at least one of the electrodes in electrical contact immediate with the calculus so as to establish a discharge channel capable to create shock waves and stresses, which excess the strength of the calculus material.

The embodiment of the invention referring to the apparatus comprises:
  a pulse generating means for generating high voltage impulses required for igniting spark discharge and producing energy sufficient for fragmenting the calculus,
  a probe for insertion within the body and transferring the energy to the calculus, said probe comprises a sheath with electrodes, which reside within the sheath, said electrodes are provided with respective distal and proximal ends, the proximal ends of said electrodes are electrically connected to the pulse generating means and the distal end of at least one of the electrodes is adapted to be in electrical contact immediate with the calculus,
  a probe manipulating means, for manipulating the sheath within the body and bringing at least one of the electrodes in electrical contact with the calculus.

The present invention and its two main embodiments have only been summarized briefly. For better understanding of the present invention as well of its embodiments and advantages, reference will now be made to the following description with reference to the accompanying drawings.

BRIEF DESCRIPTION OF THE DRAWINGS

FIG. 4b is more detailed schematics of the pulse generator, shown in FIG. 4a.

DETAILED DESCRIPTION OF SPECIFIC EMBODIMENTS

Figure 1:
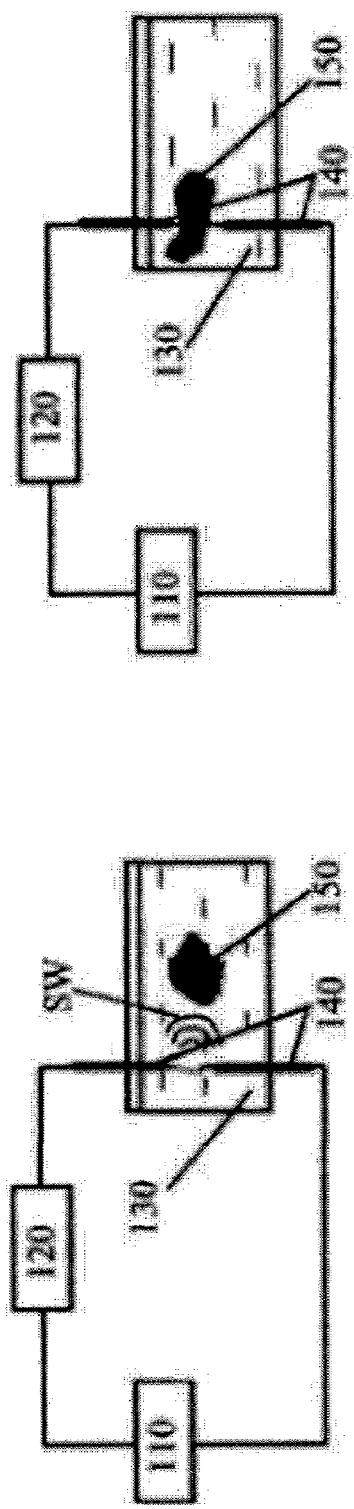
FIG. 1 shows schematically how spark discharge is initiated in electro-hydraulic lithotriptor and electro-impulse lithotriptor.

With reference to FIG. 1 the principle of operation of electro-hydraulic destruction and electro-impulse destruction can be explained as follows.

A source 110 of high voltage impulses supplies the impulses through a commutating means 120 to a working location 130, which is filled up with a working fluid and where reside electrodes 140. Igniting of spark discharge between the electrodes is used for destroying an object 150, residing at the working location. It is not shown specifically but should be understood that the object may comprise a calculus, which should be fragmented and the working location may comprise a body cavity, where the calculus is located being surrounded by the body fluid, e.g. a gull stone appearing within the gall bladder, a stone within urinary system, etc.

The left picture (a) refers to the electro-hydraulic destruction and shows that since the electrodes are not in immediate contact with the object its destruction is caused mainly due to shock waves SW caused by the spark discharge and propagating through the working liquid towards the object.

The right picture (b) refers to the principle of electro-impulse destruction and shows that the electrodes are placed immediate on the object surface to locate the spark discharge within the bulk of the object. Due to this provision the high voltage spark discharge produces spark channel within the object itself. Due to release of impulse energy within the spark channel the pressure within the channel dramatically increases, diameter of the channel enlarges causing tensile stresses within the object. The object is efficiently fragmented and destroyed due to those tensile stresses in combination with hydraulic pressure of the surrounding liquid medium and collisions with the fragments of the object.

The present invention concerns intracorporeal lithotripsy carried out in accordance with the electro-impulse principle.

It has been revealed that the probability of propagation of the spark channel through the bulk of the object increases when the speed of introducing the energy within the object increases. Practically this means that it is advantageous to apply high voltage impulses defined by very short rise time and duration. In practice it has been found that for fragmentation of wide assortment of calculi, appearing in a living body and requiring intracorporeal lithotripsy it is advantageous if the electrical impulses supplied to electrodes are defined by the following parameters: impulse rise time $t_f$ less than 50 nanoseconds, preferably less than 40 nanoseconds, duration of impulse itself $t_i$ not more than 5000 nanoseconds, preferably 500–3000 nanoseconds, impulse energy $W_0=0.1–1.0$ joule, impulse amplitude $U=5–20$ kV. The preferred configuration of the impulses is rectangular.

The pulses can be applied either as onetime impulses or as repeating impulses with frequency of several Hz.

It has been also empirically found that by virtue of supplying electro-impulses with the above parameters it is possible to destroy a calculus, having electrical strength, which is more than the pulse amplitude, since the electrical breakdown threshold against repeating impulses, is lower than the electrical breakdown threshold against a single impulse. At the same time, the energy spent for destruction is much less than the total energy of the supplied impulses, since all the impulses except the last one are associated with partial discharge.

In practice it is advantageous to supply to the electrodes high voltage impulses with positive polarity, since this is associated with increased breakdown probability.

It has been found, that by virtue of the present invention that even after applying of a single impulse or a few impulses it is possible to destroy efficiently various calculi. It can be readily appreciated that the energy level, associated with the applied impulses is about two, three and more times lower, than in the conventional electro-hydraulic lithotripsy and this is additional advantage of the invention.

Figure 2:
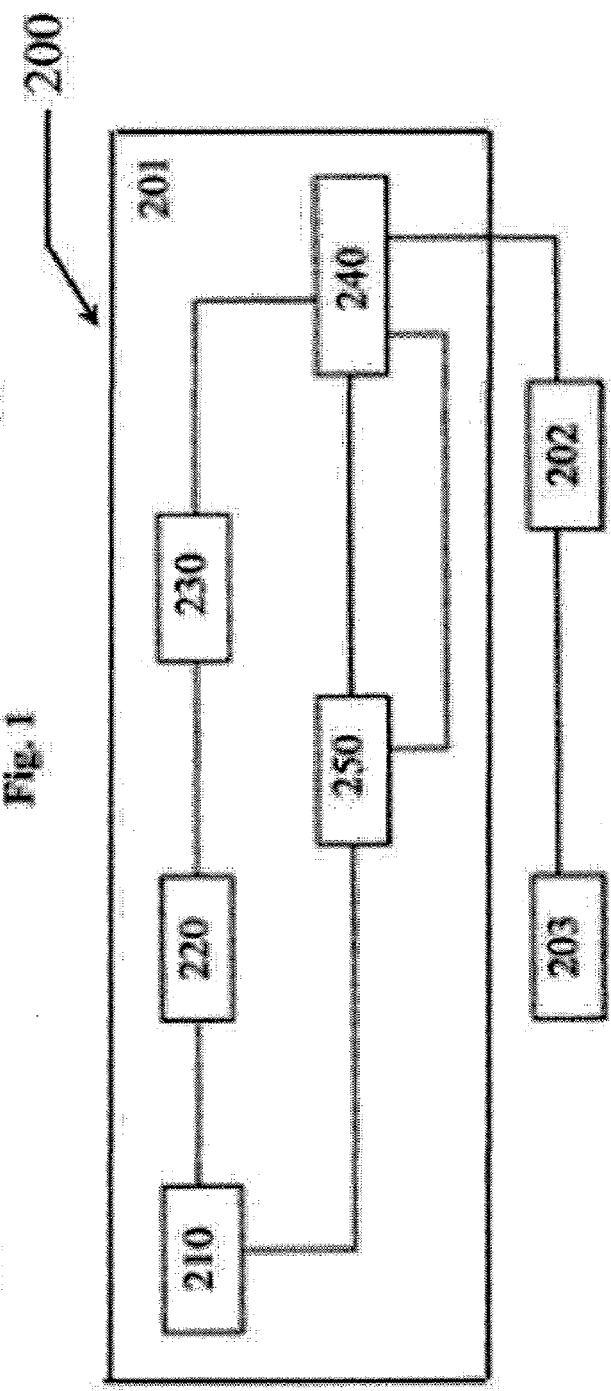
FIG. 2 is schematic block diagram of an apparatus for electro-impulse lithotripsy in accordance with the present invention.

In FIG. 2 is shown schematically an apparatus 200 for carrying out the method of intracorporeal electro-impulse lithotripsy in accordance with the present invention. The apparatus comprises a pulse generator 201, connected to a probe 203 and means 202 for manipulating the probe when it is inserted within the patient's body.

Figure 3:
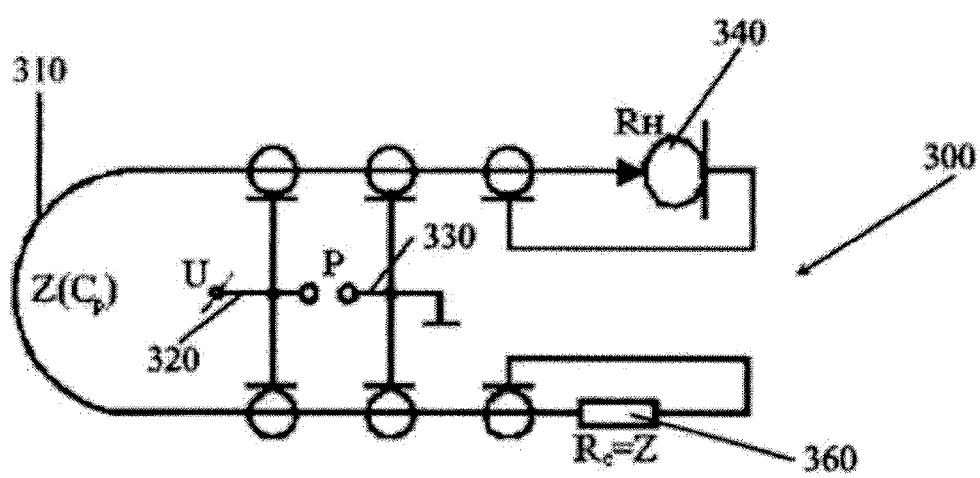
FIG. 3 shows an embodiment of the pulse generator, employed in the lithotriptor of the present invention.

The pulse generator schematic comprises the following main components: a charging means 210, an energy storage means (e.g. a capacitor) 220, a switching means 230, a pulse generating circuit 240 and a control circuit 250. As suitable charging means one can use a DC voltage or pulsed power supply and as suitable switching means one can use known in the art spark-gap and control switches, e.g. transistors, thyristors, thyrotrones and other electronic switches. The particular design of the pulse generator can vary. For example, in accordance with one embodiment of the generator, which is shown in FIG. 3 and is designated by numeral 300 the generator comprises a transmission line 310 made of coaxial cable, having fixed length, wave resistance Z and capacity $C_p$. This line is fed by a power source 320 up to a voltage $U_0$ in order to create positive wave of voltage and then to discharge this voltage via a commutating means 330 to a load 340, having resistance $R_H$, for example a calculus. The specific feature of this embodiment lies in that the beginning of the one of cable conducting wires is connected to its end and thus once the commutating means is locked the wave mode initiates simultaneously at both ends of the cable. Since the line is loaded at one of its ends with a resistance 360, which is equal to wave resistance ($R_c=Z$) the reflections do not rise at this end and there is no repeating impulses in the load 340 irrespective of its resistance $R_H$. The pulse duration in the load is equal to the time of wave propagation from one end of the line to the other. The amplitude of voltage and current in this generator is defined by the following relationships:

$$U=U_0 R_L/(Z+R_L) \quad I=U_0/(Z+R_L).$$

If $R_L=Z$, then $U=0.5U_0$ and $I=U_0/2Z$.

In this embodiment the impulse energy, which will be released on the load $R_H$ is two times less than the accumulated energy, since the load resistance Rc absorbs half of the energy.

If $R_L \gg Z$ the voltage impulse amplitude on the load approaches the feed voltage $U_0$.

In practice a coaxial cable was used with wave resistance 50 om, specific capacity 0.1 nanofarad per meter and wave propagation speed 5 nanoseconds per meter. If the cable has length 50 m then the pulse duration on the load is about 250 nanoseconds at a capacity $C_p=5$ nanofarads. The accumulated energy, defined as $W=C_P U^2/2$ varied from 0.25 to 1 joule in accordance with the voltage variation from 10 to 20 kV.

The pulse rise time on the load depends on the parameters of the switching means. In practice it was about 15 nanoseconds. It has been also found, that if $R_c \gg Z$ it is possible to achieve flat top pulse with duration of tenths of microseconds. The pulse will be terminated by a breakdown (short circuit) in the $R_L$ or will descend exponentially with a time constant $\tau=C_P R_L$ if there is no breakdown.

Now with reference to FIG. 4a another embodiment of the pulse generator means will be discussed. In this embodiment the pulse generator 400 is designed as a "concentrated capacitance". As in the previous embodiments the pulse generator is connected to a probe 420, which is manipulated by a manipulation means 410.

In this embodiment the pulse generator schematic comprises a charging means 430, connected in parallel with a first capacitor 440, which in its turn is connected via a non-controllable switch 450 with a separating inductivity 460, with a secondary capacitances 470,471,472,473 and with a transformer means, consisting of induction coils 480,481,482,483 wound around common ferrite core (not shown). The schematic comprises also a controllable switch 451, couple of current sensors 490,491 and a control circuit 495, provided with a pulse counter, indicator of pulse generation mode and indicator of breakdown mode.

Sensor 490 resides in the first winding of the transforming means and is used for counting the total amount of voltage pulses, generated during the treatment.

Sensor 491 resides in the second winding of the transformer means and senses the occurrence of breakdown between the electrodes and establishing of a spark channel. Both sensors are connected to the control circuit, which controls operation of the charging means and terminates it as soon as either a preset amount of pulses has been generated or the breakdown occurs, whatever comes first.

Figure 4A:
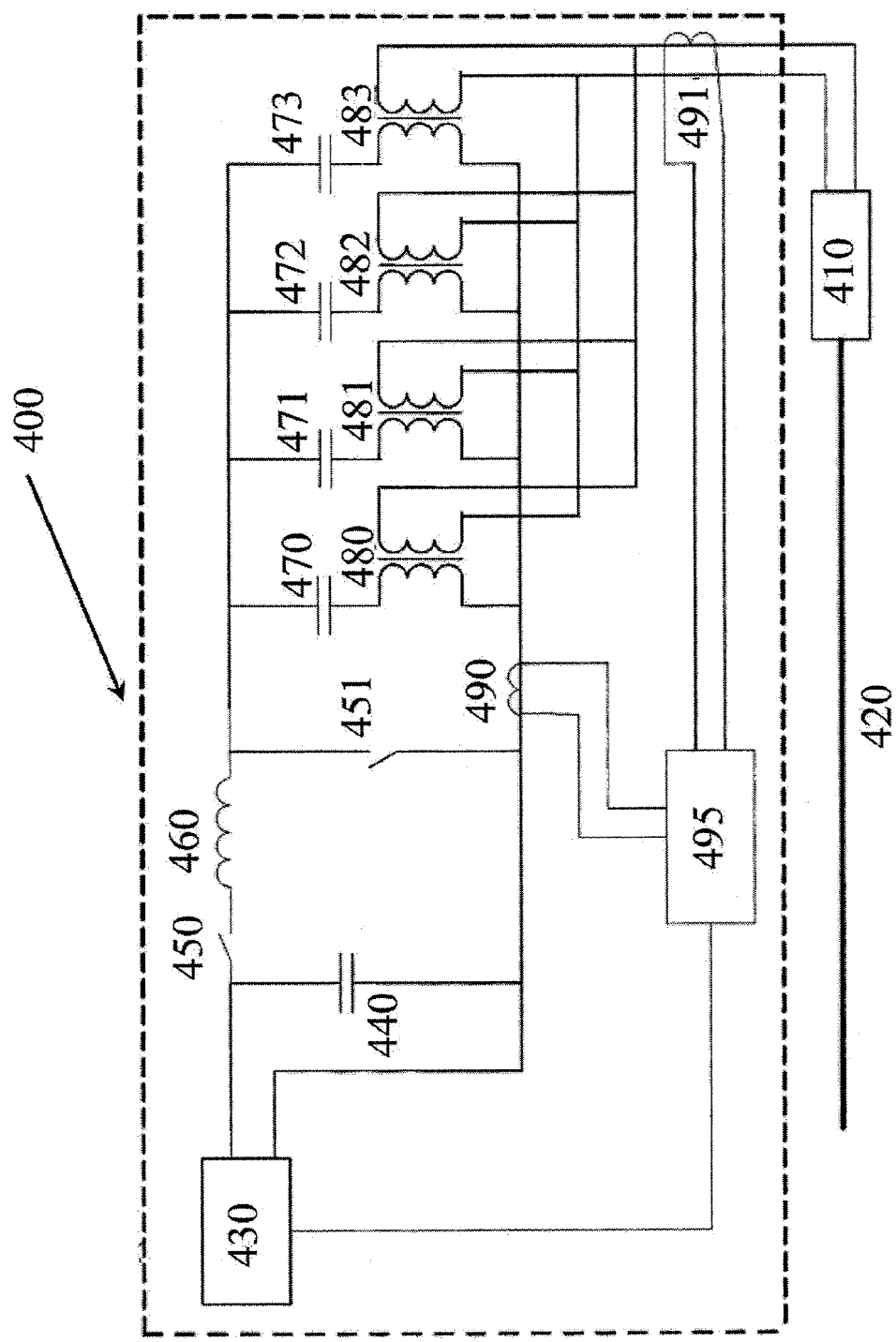
FIG. 4a shows another embodiment of the pulse generator, employed in the lithotriptor of the present invention
Figure 4B:
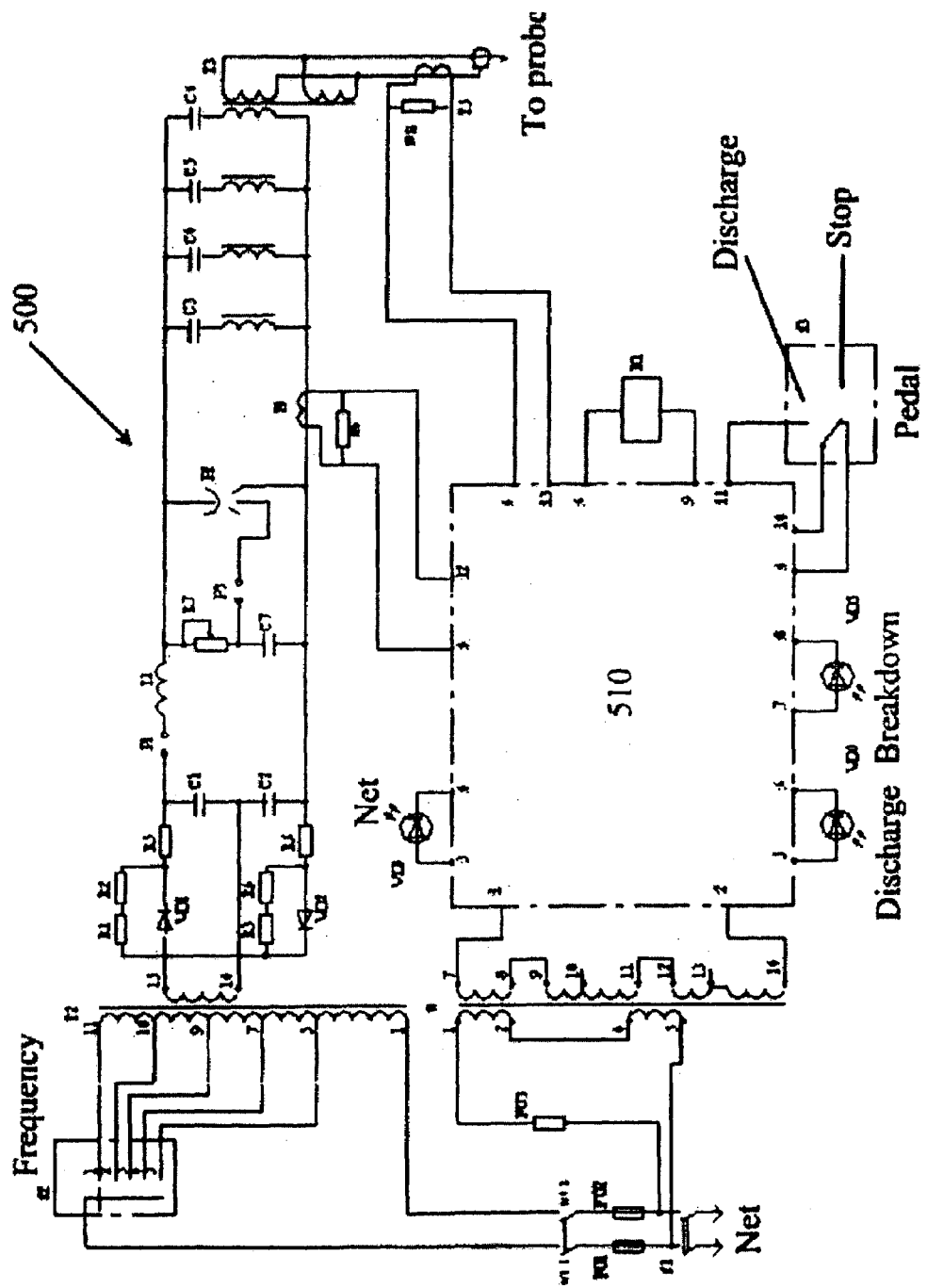

Referring now to FIG. 4b the schematics of "concentrated capacitance" embodiment will be explained in more details.

This schematics is designated by numeral 500 and comprises a group of first stage capacitors C1, C2, a separating inductive coil L1, two discharge means P1 (non-controllable) and P2 (controllable), a group of second stage capacitors C3–C6, a pulse transformer T3, elements R7, C7, P3 constituting a control circuit for discharge means P2, and induction sensors T4, T5, connected in parallel with respective resistors R9, R8.

Sensor T4 senses the impulses in the first winding of the pulse transformer T3, i.e. all the impulses delivered to the object. Sensor T5 senses the impulses in the discharge winding of the pulse transformer T3. The sensor is adjusted to detect impulses, which cause the breakdown through the object. There is provided also a dedicated microcircuit, which will be explained later on, which passes the signal, corresponding to each impulse to a pulse counter (not shown) for counting the generated impulses. In practice the pulse sensor may be a Rogovski coil or any other type suitable sensor.

A high voltage rectifier charges the first stage capacitors by means of a circuit, consisting of a transformer T2 and diodes VD1, VD2, which are shunted by resistors R1–R4. The resistors limit the pulse currents through the transistors when capacitors C1, C2 discharge.

As soon as the voltage on the capacitors is sufficient for the breakdown in the discharge means P1 the second stage capacitors are charged via inductive coil L1. Each of the capacitors C3–C6 discharges on the first winding of the pulse transformer T3 after the discharge means P2 has worked.

The amplitude and frequency of the impulses depends on the particular position of the control switch S2 and on the discharge means P1 and P2.

A control circuit 510 is provided, which is equipped, inter alia, with a relay K1 and light indicators VD3, VD4 and VD5, indicating correspondingly "Net", "Discharge" and "Breakdown". The control circuit is connected to a pedal switch S3 for switching distantly the pulse generator from the mode "Discharge" to the mode "Stop". The control circuit is connected via a transformer T1 and a switch S1 to a net supplying voltage of 220 v and frequency 50 Hz.

The generator is switched on via contacts of relay K1, which is distantly controlled by the pedal switch S3. Once the generator is switched on the light indicator VD4 lights up and shows the mode "Discharge".

Figure 5:
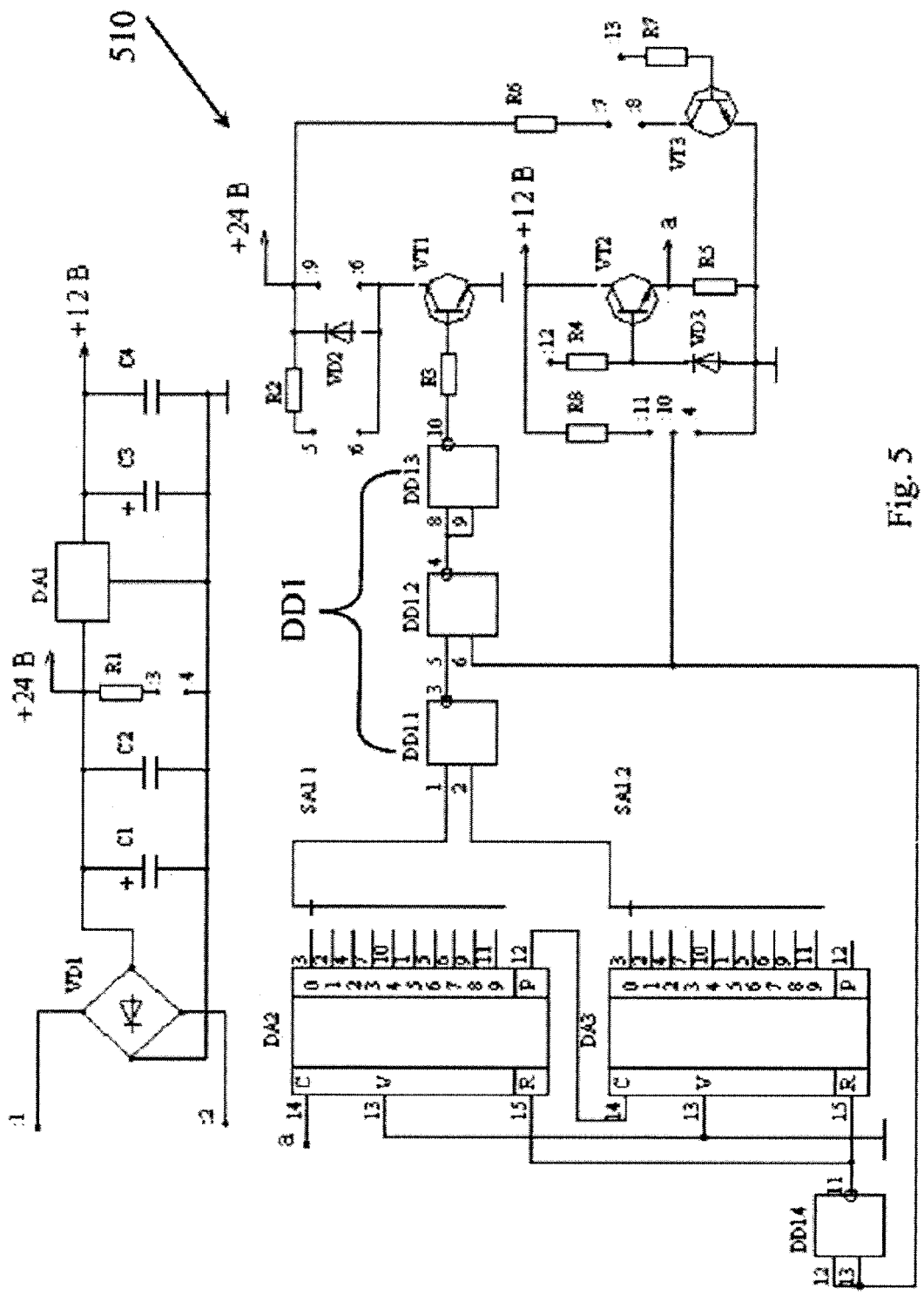
FIG. 5 depicts control circuit employed with the pulse generator, shown in FIG. 4b.

Referring now to FIG. 5 it is shown a control circuit 510, comprising inter alia a pulse counter, consisting of microcircuits DA1, DA2, transistors VT1 and VT2, and a microcircuit DD1, which compares the amount of generated pulses with the preset value. Before switching on the pulse counter is set to the required amount of working impulses between 1 up to 99.

After the generator is switched on the generated pulses are sensed by sensor T4 and transistor VT2 passes the signals associated with those pulses to the pulse counter. As soon as the amount of generated pulses reaches the preset value the microcircuit DD1 closes transistor VT1 and the generator is automatically switched off. The further functioning of the generator is possible only after repeated pushing down and release of the pedal switch S3.

Once a breakdown occurs and spark channel is established, the generation of impulses is terminated and light indicator VD5 lights up to announce this event. In this situation the pedal switch should be released to stop the generator. The calculus is observed in order to decide about the further treatment. If after observation it is found, that the calculus requires further fragmentation the generator is switched on again by onetime pushing down and release the pedal switch, each time followed by observation the calculus.

The described above pulse generator is capable to generate pulses with duration of about 1000 nanoseconds and with pulse rise time of about 50 nanoseconds and impulse amplitude in the range of 10–20 kV.

It can be readily appreciated that since the above described control circuit allows limiting the amount of pulses, which are potentially harmful for the patient it is possible to carry out the treatment more safely and at the same time more reliably.

The above-described generator employs energy storage means, which comprises capacitance. It should be understood, however, that it would be possible also alternative storage means, for example comprising inductive means.

In accordance with the invention one can contemplate various modes of electrical contact between the electrodes and the object.

Figure 6:
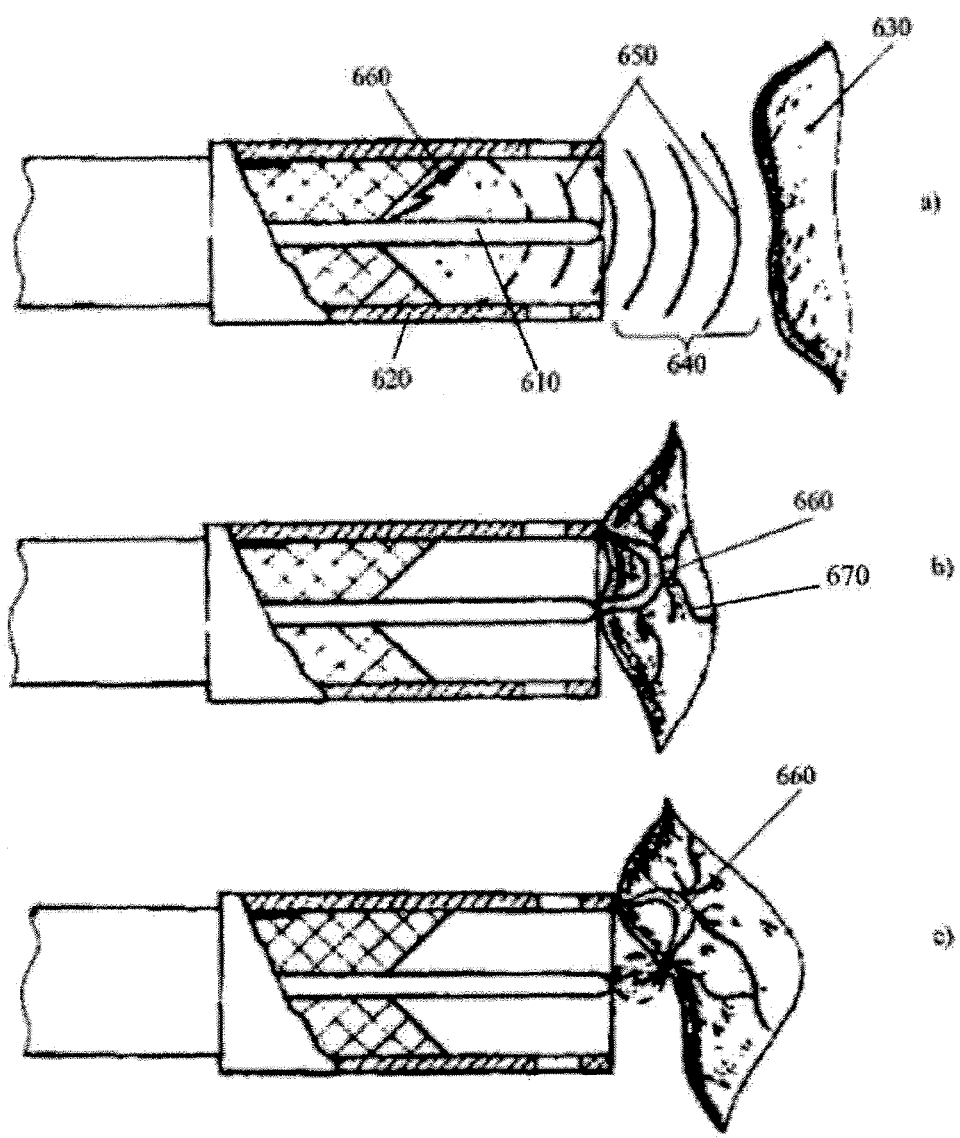
FIGS. 6a–6c show schematically principle of electro-hydraulic and electro-impulse lithtripsy FIGS. 7–10 refer to various embodiments of a probe, employed in the lithotriptor of the present invention.

With reference to FIG. 6 it is shown schematically various modes of spark discharge propagation depending on the disposition of the electrodes with respect to the object to be fragmented. FIG. 6a refers to conventional electro-hydraulic destruction and shows schematically a high voltage central electrode 610, which is surrounded by a second annular electrode 620, formed as a tubular member concentric with the first electrode. An object 630, e.g. a calculus is seen, which is distant from both electrodes and due to a gap 640 none of the electrodes is in immediate electrical contact with the calculus. Shock waves 650 produced by a spark discharge 660 propagate towards the calculus. No discharge channel is formed in the calculus.

In FIG. 6b is seen that both electrodes are brought in immediate electrical contact with the calculus and there is no more gap therebetween.

A discharge channel 660 originates between the electrodes within the bulk of the object and causes its destruction due to formation of plurality of small cracks 670.

Figure 7:
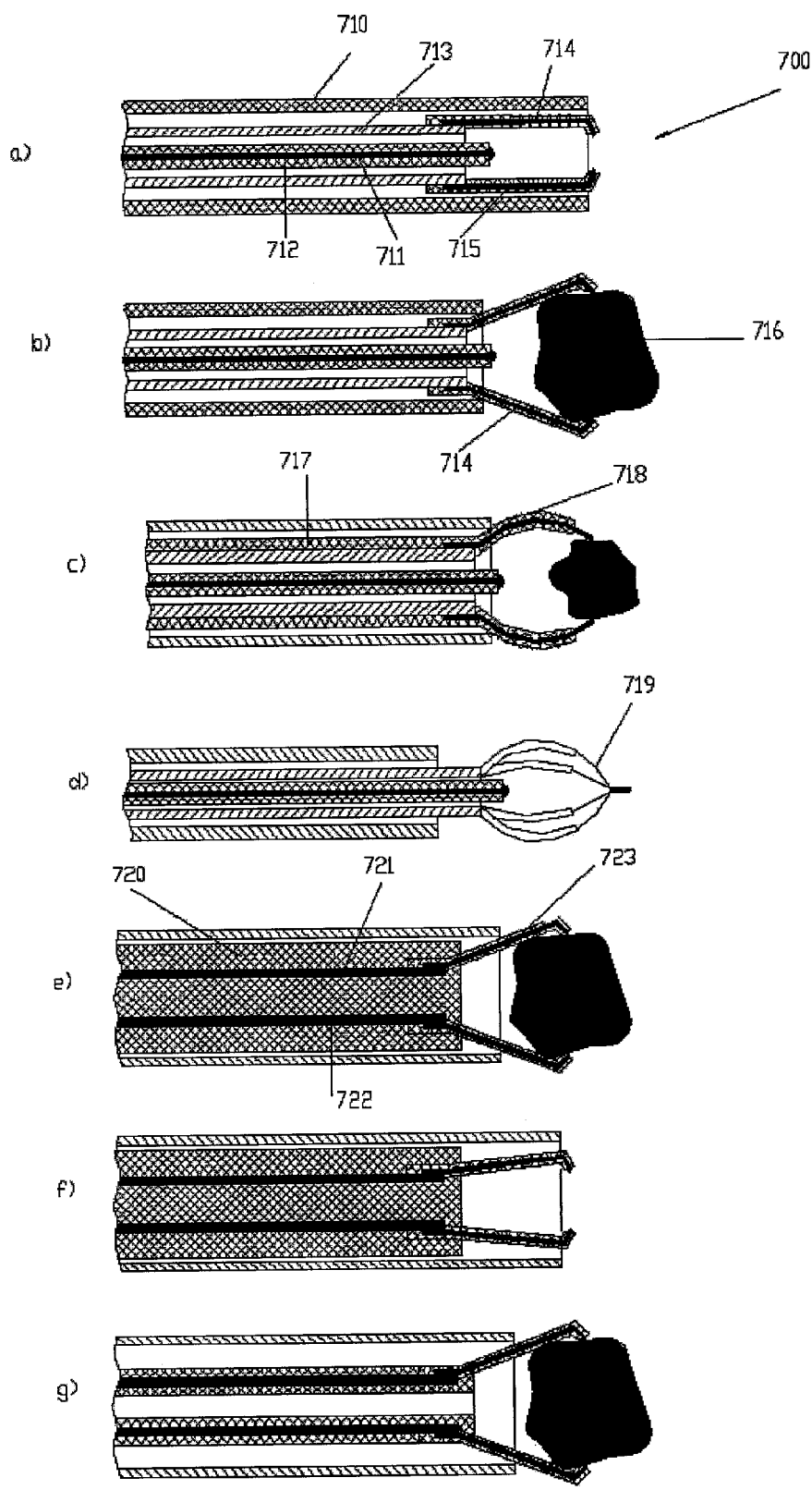

In FIG. 6c is seen how only the second electrode is brought in immediate electrical contact with the object, while the central electrode is kept distant therefrom. Nevertheless, the discharge channel is still formed within the bulk of the object and causes its destruction. Now with reference to FIGS. 7 a–d it will be described the probe for electro-impulse lithotripsy treatment, which enables immediate electrical contact with the object to be fragmented in accordance with the mode, shown in FIG. 6b.

The first embodiment of the probe is designated by numeral 700. In this embodiment the probe itself comprises a tubular sheath 710, through which extends a high voltage central electrode 711, electrically insulated from the interior of the sheath by an insulation covering 712. It is advantageous if the sheath 710 is made of dielectric material, however it might be made alternatively from electrically conductive material, covered by insulation coating. A second electrode 713 is provided. This electrode comprises tubular member, which resides within the sheath coaxially and concentrically with the central electrode.

The distal extremity of the second electrode is provided with a couple of elastic contacts 714, which are electrically insulated by an insulation coating 715. Both electrodes reside within the sheath with possibility for their independent linear displacement along the longitudinal axis of the probe from a fully retracted position, in which the electrodes are contained entirely within the sheath to a fully protracted position, in which the electrodes are outside the sheath. When in protracted position the electrodes can approach the outside surface of a calculus to be fragmented and then high voltage impulses can be supplied to the electrodes from the pulse generator.

It is not shown specifically but should be realized, that proximal extremities of the electrodes are operatively connected to a mechanism for linear displacement, which is referred in FIGS. 2, 4a as probe manipulating mean 202 and 410 respectively. It should be understood that the displacing mechanism might comprise any suitable means, conventionally used in lithotriptor devices for manipulating the probe.

Also it is not specifically shown in FIG. 7a, that one of the electrodes is electrically connected to the pulse generator to receive high voltage impulses with the above-described parameters and the other electrode is grounded.

In FIG. 7a is depicted the situation when both electrodes are still in their retracted position within the sheath and are about to exit from the sheath.

In FIG. 7b is seen that the second electrode is brought in the most protracted position, in which its elastic contacts 714 approach a stone 716 and are in immediate electrical contact therewith. The central electrode is still within the sheath and is ready to be protracted towards the stone to establish electrical contact with it.

In accordance with the invention the amount and specific configuration of elastic contacts might be different. In practice the contacts are made of biologically inert, elastic and electrically conductive material, e.g. TiNi or any other suitable material, including so called memory shape alloys. Insulating coating covers the contacts except of their tips, which should contact the stone.

In the embodiment shown in FIG. 7a the elastic contacts are provided with rectilinear configuration and their tips are bent at an acute angle with respect to the longitudinal axis of the probe. By virtue of this provision it is possible to enable better grasping and containment of the stone and at the same time to ensure reliable electrical contact with its surface.

In FIG. 7c is shown alternative embodiment of the probe in which the sheath is made of electrically conductive material and the second electrode is covered by an insulation coating 717. The distal extremity of the second electrode is provided with a couple of elastic contacts 718, which have arcuate configuration.

In FIG. 7d is shown still further embodiment in which the elastic contacts of the second electrode comprise a retrieval basket 719 suitable for immobilization of the stone and retaining thereof during the treatment. An example of such a basket is described in our previous patent application PCT/IL01/00591 herein incorporated by reference.

Still another embodiment of the probe is shown in FIG. 7e. In this embodiment the sheath is made of metallic material and instead of two concentric electrodes a single symmetric cable 720 is used, which is placed within the sheath with possibility for linear displacement along the sheath. The cable is provided with two conducting wirings 721,722, connected at their proximal ends to the pulse generator (not shown). Distal ends of the electrodes connected, e.g. by soldering to elastic contacts 723, for example similar to those, which have been already mentioned. FIGS. 7e, f respectively show the probe provided with the two-wire cable when it is in protracted and retracted position.

Still further embodiment of the invention is shown in FIG. 7g, in which for supplying impulses two separate insulated wirings are used instead of a single symmetrical cable. These two insulated wirings may be parallel one to another or twisted between them. As in the previous embodiment the elastic contacts are connected to the distal ends of both wirings and their configuration is suitable for grasping the stone and establishing immediate electrical contact therewith.

In practice the electro-impulse lithotriptor of the invention should be used in combination with an endoscope, equipped with suitable optics enabling monitoring the procedure within the living body. The endoscope is introduced in the body before the probe and is brought proximate to the calculus. After that the probe is entered and brought near to the calculus. Once the probe resides in the required position its electrodes are protracted from the probe by the displacement mechanism until they touch the calculus. If the probe consists of two concentric electrodes the second electrode, carrying the elastic contact is protracted first and after that the central electrode. Once the calculus is grasped by the contacts the pulse generator is switched on and voltage impulses with the above-mentioned parameters are supplied to the electrodes to ignite spark discharge, resulting in propagating of discharge channel through the bulk of the calculus, which results in destroying the calculus.

Figure 8A:
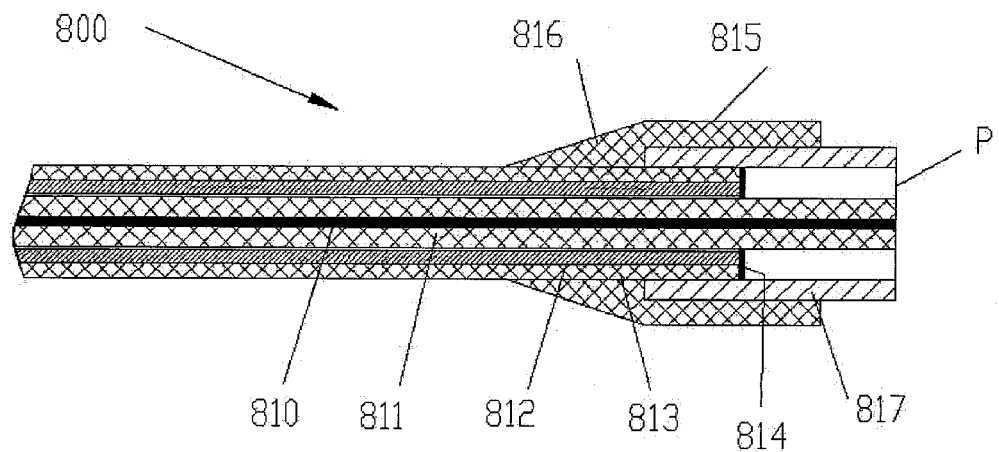
Figure 8B:
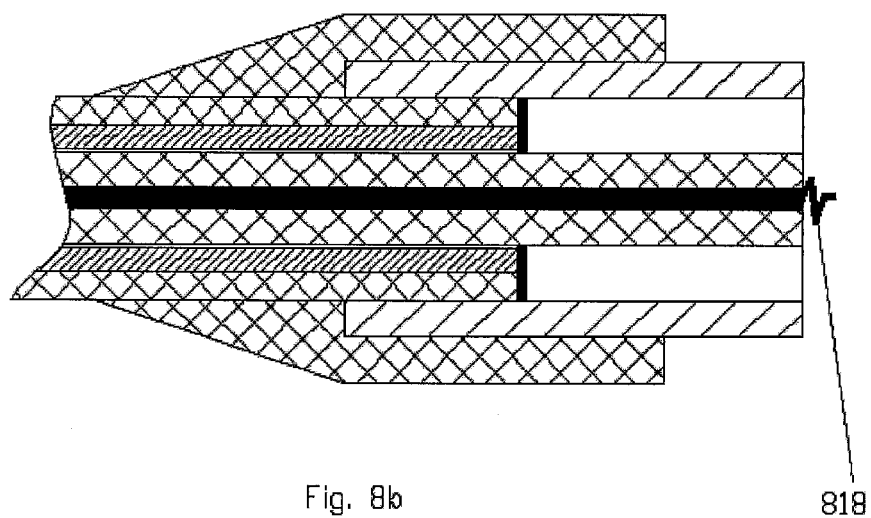

Referring now to FIGS. 8a–c still further embodiments of the probe will be explained. These embodiments are suitable for establishing electrical contact with the object in accordance with the mode shown in FIG. 6c.

As in the previous embodiments a probe 800 is provided with a high voltage central electrode 810, extending along the probe and insulated therefrom by a sleeve 811 made of a dielectric material, e.g. TEFLON or FEP or PTEE, or any other suitable material, which is mechanically resistant to shocks waves, developed during the treatment.

Figure 9:
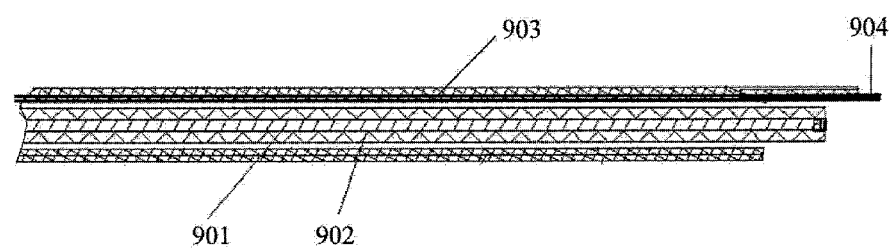
Figure 9:
Figure 9:
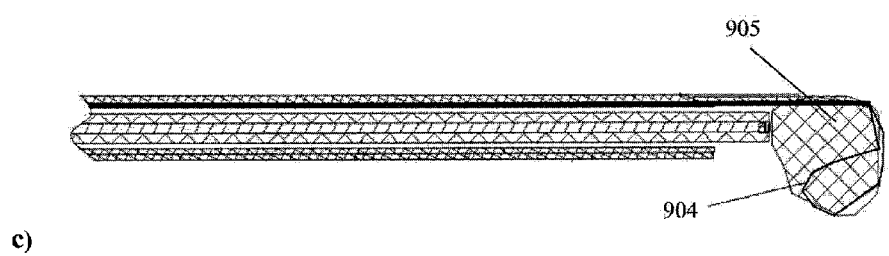

The forwardmost end of the central electrode is exposed to allow electrical contact with the object to be destroyed (not shown) as soon as the electrode is brought in physical contact therewith. A second electrode 812 is provided, which has cylindrical shape and resides concentrically with the central electrode. The second electrode is electrically insulated from the interior of the probe by an insulation covering 813 also made of a dielectric material. In contrast to the previous embodiments the second electrode is not provided with elastic contacts or basket or any other means, enabling gripping and containment of the object. Instead of this to the forwardmost end of the second electrode is attached a washer 814, which is made of an electrically conductive material. To the proximal extremity of the probe is attached a mouthpiece member, having a cup-like forward portion 815 and a skirt-like rear portion 816. The inside diameter of the forward portion exceeds the outside diameter of the probe and there is provided an annular space therebetween. A short bushing 817 made of electrically conductive material resides in the annular space to enable electrical contact with the second electrode via the washer. The length of the bushing and of the rear portion of the mouthpiece member are selected in such a manner, that the forward most end of the central electrode and the forward most end of the bushing lie in the same plane P and constitute working electrodes. In practice it is required, that the length of contact between the bushing residing within the mouthpiece member and the probe is 4–6 mm. Once the probe is brought to the object and working electrodes touch it an electrical contact can be established in accordance with the mode shown in FIG. 6b or FIG. 6c. It can be readily appreciated, that by virtue of the embodiment shown in FIG. 8a it is possible to localize the spark channel at the very end of the probe and thus to allow its propagation either through the surface of the object, or through its bulk, and thus to ensure much more efficient destruction than in conventional electro hydraulic lithotripsy. With reference to FIG. 8b still further embodiment of the probe is shown, in accordance with which an auxiliary contact 818 made of resilient refractory material is secured on the forwardmost end of the central electrode. Examples of suitable material for auxiliary contact comprise TiNi, stainless steel etc. Due to this contact the probability of propagation of the spark channel through the object improves and so the service life of the probe. Still further embodiment of a probe provided with a contact element made of electrically conductive super elastic material (e.g. stainless steel) or of a shape memory alloy (e.g. NiTi) is shown schematically in FIGS. 9 a,b,c.

The probe is formed with a central electrode 901 electrically insulated by a coating 902 from a second electrode 903, which is parallel to the central electrode. The second electrode is displaceable along the probe and to its forward most end is attached a loop-like contact element 904, made of narrow strip or filament. This contact element is capable to bend around the calculus when the second electrode is in protracted position shown in FIG. 9b. The central electrode is also displaceable along the probe and once it is brought in contact with a calculus 905 the contact element starts bending around the calculus as seen in FIG. 9c to allow the loop reliably contact with the calculus. The bending is possible either due to super elasticity of the loop itself or, when it is made of a memory shape alloy, by virtue of small voltage applied thereto.

Figure 10:
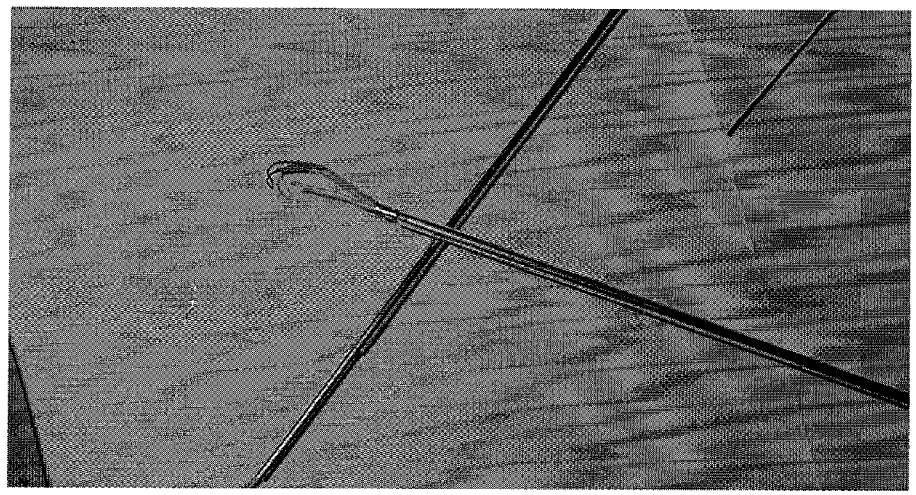
Figure 10:
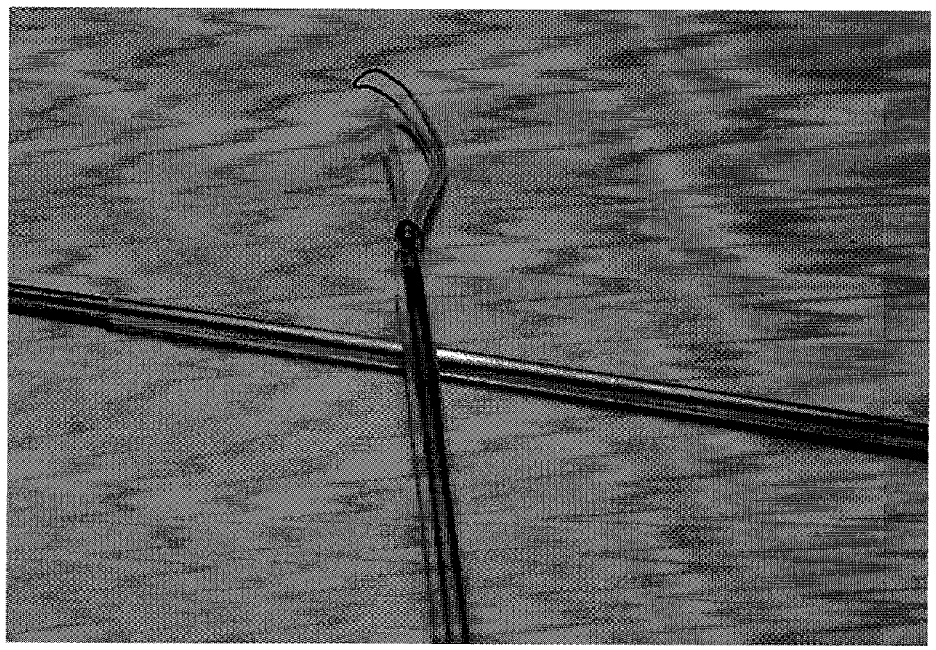

Examples of a real probe, made in accordance with this embodiment are seen in FIGS. 10 a,b.

By virtue of the invention it is possible to fragment various calculi in the body more efficiently by applying energy, which is several times less, than in conventional electro-hydraulic intracorporeal lithotripsy. This becomes possible, since the fragmentation is caused by tensile stresses, caused by propagation of the spark channel, which goes through the surface or the bulk of the calculus.

Furthermore, since the fragmentation can be carried out selectively by applying desired amount of impulses instead of plurality of high frequency impulses the treatment is safer for the patient, and the probability for traumatizing adjacent body tissues is less.

It can be also appreciated that since the amount of high voltage impulses required for producing electrical breakdown between the electrodes can be preset in advance, the contacts wear less and thus the probe service life is longer.

The probe construction is simple and therefore reliable. It allows grasping and containment of the calculi during the treatment and this also contributes to the reliability of the treatment.

It should be understood that the present invention should not be limited to the above described example and embodiments. One ordinarily skilled in the art can make changes and modifications without deviation from the scope of the invention. For example, as a sensor for sensing the generated impulses one can use an inductive or capacitive sensor, instead of a current sensor for detecting the breakdown event one can use an inductive sensor, or a capacitive sensor, or a resistive sensor etc.

The specification referring to FIG. 4b does not disclose in details the particulars of various components shown, e.g. diodes, resistances, integrated circuits, since selecting of these particulars lies within routine work, required from one skilled in the art.

It should be appreciated that the features disclosed in the foregoing description, and/or in the following claims, and/or in the accompanying drawings may, both separately and in any combination thereof, be material for realizing the present invention in diverse forms thereof.

What is claimed is:

1. A method for fragmenting of various calculi in a living body by intracorporeal lithotripsy treatment, during which a probe is brought to the calculus to be fragmented, said probe is provided with electrodes, connected to a means for generating of high voltage impulses, said impulses are supplied to the electrodes for igniting spark discharge between them and release of energy, causing fragmenting of the calculus, wherein the method comprises bringing of at least one of the electrodes in electrical contact immediate with the calculus so as to establish a discharge channel capable to create shock waves and stresses, which excess the strength of the calculus material, wherein said high voltage impulses are defined by the following parameters: impulse rise time $t_f$ less than 50 nanoseconds, duration of impulse itself $t_i$ not more than 5000 nanoseconds, impulse energy $W_O$=0.1–1.0 joule, impulse amplitude U=5–20 kV.

2. The method as defined by claim 1, in which said impulses are supplied as single impulses.

3. The method of claim 1, in which said impulses are supplied as repeating impulses with frequency of up to several tens of Hz.

4. The method of claim 1, in which said impulses are defined by the following parameters: impulse rise time $t_f$ less than 40 nanoseconds, duration of impulse itself $t_i$ not more than 3000 nanoseconds.

5. The method of claim 4, in which the amplitude of said impulses, is below the value of single pulse breakdown threshold of the calculus.

6. The method of claim 1, comprising sensing the onset of the electrical breakdown, associated with fragmenting of the calculus.

7. The method of claim 6, comprising termination of the generation of the high voltage impulses as soon as the onset of the electrical breakdown is sensed.

8. The method of claim 7, comprising presetting certain amount of high voltage impulses to be supplied to the electrodes, counting the amount of impulses actually generated by the generator and termination the generation as soon as either the preset amount is achieved or the electrical breakdown is sensed.

9. The method of claim 1, comprising grasping the calculus before supplying the impulses and its containment during supplying the impulses.

* * * * *